United States Patent [19]

Sarnoff

[11] Patent Number: 4,661,469

[45] Date of Patent: Apr. 28, 1987

[54] T-PA COMPOSITION CAPABLE OF BEING ABSORBED INTO THE BLOOD STREAM AND METHOD OF ADMINISTRATION

[75] Inventor: Stanley J. Sarnoff, Bethesda, Md.

[73] Assignee: Survival Technology, Inc., Bethesda, Md.

[21] Appl. No.: 708,845

[22] Filed: Mar. 6, 1985

Related U.S. Application Data

[63] Continuation-in-part of Ser. No. 638,695, Aug. 8, 1984.

[51] Int. Cl.[4] .................. A61K 31/00; A61K 33/02
[52] U.S. Cl. ........................................ 514/2; 424/166
[58] Field of Search ............................ 424/166; 514/2

[56]  References Cited

PUBLICATIONS

Iizuka et al–Chem. Abst., vol. 77 (1972) p. 17315u.
Korninger et al–Chem. Abst., vol. 95 (1981) p. 197233u.
Belousov et al–Chem. Abst., vol. 92 (1980) p. 39285w.
Levin, Proc. Natl. Acad. Sci., USA, vol. 80, pp. 6804–6808, Nov. 1983.

Primary Examiner—Sam Rosen
Attorney, Agent, or Firm—Cushman, Darby & Cushman

[57]  ABSTRACT

The absorption rate of t-PA in the blood is enhanced by administering it together with an absorption enhancing agent, preferably hydroxylamine or a salt thereof, most preferably hydroxylamine hydrochloride.

7 Claims, 5 Drawing Figures

T-PA COMPOSITION CAPABLE OF BEING ABSORBED INTO THE BLOOD STREAM AND METHOD OF ADMINISTRATION

This application is a continuation-in-part of application 638,695, filed Aug. 8, 1984, the entire disclosure of which is hereby incorporated by reference and relied upon.

This invention relates to the treatment of coronary prone individuals in the throes of a suspected myocardial infarction in such a way as to minimize damage to the heart muscle and, more particularly, to improvements in such treatments enabling the same to be commenced at the earliest possible time, even before direct qualified personal care of the individual can be established.

When a clot forms in a blood vessel, the body organ being supplied with blood by that blood vessel is compromised or totally deprived of blood supply. Depending on the blood vessel in which this occurs, the threat to the life of the individual is either small or very great as in the circumstances to be addressed by the material below, i.e. certain life threatening circumstances. Clot formation in a vessel is described as thrombosis. Substances which dissolve thrombi are called thrombolytic substances. When a coronary artery clot is dissolved, the resultant establishment of blood flow to the heart is called reperfusion.

Examples of life threatening or very serious clot formation in arterial vessels are cerebral thrombosis, renal thrombosis, opthalmic artery thrombosis, and very importantly, thrombosis of a coronary artery. In approximately 85% to 90% of cases of acute myocardial infarction (coronary heart attack), a thrombus is found in the coronary artery preventing blood from flowing to the heart muscle (myocardium) and supplying it with essential oxygen and other nutrients. A consequence of a thrombus or clot forming in a coronary artery is the danger to the myocardium (heart muscle tissue that does the pumping of blood). Heart muscle deprived of it's blood supply does not die immediately but does promptly begin the process of becoming dead. The extent of the damage which is done to the heart muscle is, therefore, a function of the time during which the supply of blood to the infarct zone is restricted by the occluding thrombus Heretofore, the procedures undertaken to actually establish reperfusion to the infarct zone have generally been undertaken in a hospital environment or equivalent. The so-called "prehospital" treatment was, in general, directed toward keeping the patient alive and getting the patient into the hospital environment as soon as possible so that treatment minimizing the heart muscle damage could be accomplished.

The treatment undertaken in the hospital environment involves certain procedures for establishing reperfusion in the infarct zone of the patient's heart. When immediate surgery was not clearly indicated, the establishment of reperfusion was accomplished by procedures which had the effect of unblocking the occlusion. The available procedures included mechanical catheterization and the administration of thrombolytic agents. Known thrombolytic agents, such as streptokinase or urokinase required intracoronary infusion or the slow infeed of the agent within the vessel at the site of occlusion by means of a catheter. In recent years, intravenous infusion of streptokinase has been shown to be effective.

More recently a substance called tissue-type plasminogen activator or t-PA has been utilized experimentally. (*The New England Journal of Medicine*, Mar. 8, 1984, Volume 310, No. 10, pages 609–613). Unlike other plasminogen activators, such as streptokinas or urokinase, t-PA—which is found in only small amounts in the body—acts specifically on clots and not on other relevant proteins in the blood, when maintained at appropriate and effective levels.

A 1984 Commentary found in *Biochemical Pharmacology*, Volume 33, No. 12, pages 1831–1838 entitled "Coronary Thrombolysis: Pharmacological Considerations With Emphasis On Tissue-Type Plasminogen Activator (t-PA)" contains the following conclusionary statement:

"Selection of pharmacological agents for induction of coronary thrombolysis has been determined largely by availability. Unfortunately, both streptokinase and urokinase induce a systemic lytic state with depletion of circulating fibrinogen, plasminogen, and α 2-antiplasmin, and accumulation of fibrin degradation products. All of these factors conspire to set the stage for hemorrhage with a risk of serious bleeding. Intravenous administration of these agents is limited by a lower success rate, in part because the upper bound of dose is constrained by the risk of inducing a severe systemic lytic state.

The probability that progress in recombinant DNA technology will lead to widespread availability of tissue-type plasminogen activator is particularly exciting because of the clot specific properties of t-PA. For coronary thrombolysis its potential advantages include: safety and efficacy of intravenous administration of high doses; effective clot lysis without induction of a systemic lytic state; prompt implementation without the need for extensive characterization of the coagulation and fibrinolytic systems in each patient prior to and during therapy; avoidance of frank allergic reactions or variations in dose-response relation due to immune complex formation; ease of minute-by-minute adjustment of dosage and prompt termination of fibrinolysis when needed because of the short biological half-life of t-PA and the lack of induction of a systemic lytic state."

The promise attributable to t-PA administration was discussed at a news conference at a meeting of the Americal Heart Association and reported by the *New York Times* on Nov. 16, 1983, in an article entitled, "Protein Of Cancer Cells Used To Halt Coronaries." The article refers to injection of t-PA by stating the following: "The protein t-PA can simply be injected into the vein in the arm of the patient seized by a myocardial infarction or heart attack, and it travels through the blood to dissolve a clot, in much the same way as Draino clears up stopped plumbing."

The article further indicated under the subheading "Hopes For Future Application" that many physicians have expressed excitement about research into the use of t-PA to treat heart attacks because they hope that some day it may be used in emergency rooms and ambulances to stop heart attacks at their earliest stages before they kill or cause permanent damage. Under the "Hopes For Future Application" subheading there is also included the following paragraph: "Dr. Burton E. Sobel Of Washington University, one of the researchers, speculated that patients might some day carry a vial with them so that the drug could be injected immediately after they felt chest pain and other early symptoms of a heart attack."

In medical parlance, a vial is a container for a quantity of liquid medicine or diluent having a rubber stopper capable of being pierced by a hypodermic needle of a syringe to enable the operator of the syringe to withdraw a predetermined dosage of the liquid from the vial. In the case of t-PA as currently used, the dosage could then be injected into the mother liquid container of an infusion assembly. The necessity to administer the drug by intravenous infusion or by intravenous injection presents a significant barrier to self-administration from a practical view point, particularly when considering the disconcerting circumstances of the individual undergoing the symptoms of a myocardial infarction.

The development of an effective self-administration procedure for t-PA sufficient to enable its utilization by a targeted coronary prone individual immediately following onset of symptoms, would materially increase the potential efficacy of t-PA as a thrombolytic agent by insuring its use at the earliest possible time often before irreversible heart muscle damage has occurred, and, at the same time, provide a treatment of the pre-hospital or pre-ambulance type which for the first time is directly effective to minimize heart muscle damage accompanying myocaridal infarction. It is an object of the present invention to provide such a self administering treatment.

Another object is to enhance the absorption rate of t-PA in the blood when introduced intramuscularly.

The invention includes packaging t-PA and an agent enhancing the absorption of t-PA in the blood. The agent preferably is hydroxylamine hydrochloride, in a known emergency type automatic injector and injecting the two medicament agents into the muscle tissue, e.g. after having received a decision to do so over the telephone from a qualified source and at a time prior to the establishment of direct contact qualified personal care.

Even though t-PA may be regarded as a clot selective thrombolytic agent, when introduced into the blood stream at a predetermined level, tests thus far performed show that the concentration can be increased to the point that a systemic lytic state can be induced. Intramuscular injection involves the introduction of concentrated dosage of t-PA in an area contiguous to and substantially surrounding the wound caused by the penetration and withdrawal of the injection of the hypodermic needle. Consequently, it would be expected that at least a localized lytic state would be induced resulting in hemorrhage from the needle wound. Unexpectedly, tests have shown that no such hemorrhage does in fact occur.

Second, t-PA is a large protein. It would not be expected that it would be absorbed into the blood stream in discernible quantities. Extravascular levels of protein are about 1/10 that of intra-vascular protein. It is thought that this is so because the capillary pores through which transport of protein can occur are small relative to the molecular size of protein and limit protein transport because of electrical charge. It was thus highly problematical as to whether a large protein such as t-PA, when given intra-muscularly, i.e. outside the blood vessels, would find its way rapidly into the blood stream in discernible quantities. Application tests have indeed shown that by itself t-PA does not find its way rapidly into the blood stream in therapeutically significant quantities after intramuscular injection.

The actual treatment of the system must therefore include intramuscular injection of an absorption enhancing agent simultaneously or substantially simultaneously with the intramuscular injection of the t-PA so as to produce effective thrombolytic blood levels.

Augmentation of absorption of low molecular weight substances administered topically, subcutaneously, or intramuscularly has been achieved with vehicles such as dimethylsulfoxide (DMSO) and by enhancement of skeletal muscle blood and lymph flow.

However, DMSO has proven ineffective as an absorption enhancing agent for t-PA.

In accordance with the principles of the present invention, the absorption rate of t-PA in the blood is enhanced by utilizing with the t-PA dosage, a dosage of an absorption enhancing agent for t-PA, preferably hydroxylamine hydrochloride. Preferably, the absorption enhancing agent such as hydroxylamine hydrochloride is mixed in with the t-PA dosage to form a single mixed dosage which is then injected intramuscularly (i.m.), e.g. as described in the parent application. Through the contemplation of the present invention to inject the absorption enhancing agent as a separate dosage within the same site as the separate dosage of t-PA, (e.g. U.S. Pat. No. 4,394,863). An example of an amount of absorption enhancing agent, such as hydroxylamine hydrochloride, which is added to the t-PA dosage, as previously described, to form a single mixed dosage is an amount of from 0.1 to 85 e.g. 0.1 to 40 or 1 to 85 milligrams per kilogram of body weight.

As the absorption enhancing agent hydroxylamine is preferably employed in the form of a non-toxic water soluble salt. Thus there can be used for example in place of hydroxylamine salts such as hydroxylamine hydrochloride, hydroxylamine hydrobromide, hydroxylamine hydroiodide, hydroxylamine sulfate, hydroxylamine nitrate, hydroxylamine acetate, and hydroxylamine propionate. Most preferably there is employed hydroxylamine hydrochloride.

There is also contemplated as absorption enhancing agents for t-PA in accordance with the invention compounds such as ammonia (ammonium hydroxide), ammonium carbonate and other ammonium salts, e.g. ammonium chloride, ammonium acetate, ammonium bromide and ammonium sulfate, urea, mono and dialkyl ureas, e.g. methyl urea, ethyl urea, propyl urea, butyl urea, N,N-dimethyl urea, N,N-diethyl urea, N,N-diisopropyl urea, mono and diaryl ureas, e.g. phenyl urea, p-tolylurea, N,N-diphenyl urea and, N,N-di-p-tolyl urea, thiourea, hydantoin, 5-substituted hydantoins, e.g. 5-alkyl, 5-aralkyl, and 5-aryl hydantoins and 5,5-dialkyl and 5,5-diaryl hydantoins, e.g. 5-methyl hydantoin, 5-ethyl hydantoin, 5,5-dimethyl hydantoin, 1,5-trimethylene hydantoin, 1,5-tetramethylene hydantoin, 5-phenyl hydantoin, 5-p-tolyl-hydantoin, and 5,5-diphenyl hydantoin, guanidine, methyl guanidine, hydrazine, alkyl and aryl hydrazines, e.g. methyl hydrazine, ethyl hydrazine, butyl hydrazine, phenyl hydrazine and diphenyl hydrazine, alkyl and aryl hydroxylamines, e.g. methyl hydroxylamine, ethyl hydroxylamine and phenyl hydroxylamine. The substituted ureas, hydrazines and hydroxylamines likewise can be used in the form of salts, e.g. as hydrochlorides.

Also while the simultaneous administration of t-PA and absorption enhancing agent is primarily intended for human use, it is within the scope of the invention that they be administered to other mammals, e.g. dogs, cats, cattle, and horses.

It is known that hydroxylamine, e.g. as the hydrochloride, dissociates t-PA from its naturally occurring inhibitor in tissue culture, Levin. Proc. Natl. Acad. Sci. USA 80, 6804–6808 (1983). It is also known that hydroxylamine inhibits platelet aggregation, see Iizuka, Chem. Pharmacol. Bull. 20 614–616 (1972) and elicits smooth muscle relaxation potentially enhancing vasodilation and hence absorption at the injection site, see Diamond, J. Pharmacol, Exp. Therap. 225, 422–426 (1983). These properties may contribute to its success in the present invention.

While t-PA and the absorption enhancing agent would usually be administered intramuscularly they can also be administered singly or in combination intravenously since hydroxylamine has been shown (see Levin, loc. cit) to disassociate t-PA inhibitor from t-PA, thereby enhancing the effect of the infused exogenous t-PA or the hydroxyl amine and thus reducing the amount of t-PA required to accomplish thrombolysis. As pointed out above the hydroxylamine will usually be administered in the form of a non-toxic salt, preferably the hydrochloride. The dosage of absorption enhancing agent, e.g. hydroxylamine hydrochloride can be in the range previously mentioned. In place of hydroxylamine in this phase of the invention there can be added other t-PA inhibitor disassociating agents. In accordance with the teachings of my copending U.S. application 460,011, filed Jan. 21, 1983 (the disclosure of which is hereby incorporated by reference into the present specification), electrical stimulation of the muscle at the injection site was employed in concert with the inclusion of an absorption-enhancing agent, specifically hydroxylamine hydrochloride, in the injectate in a number of the following examples using intramuscular injection. Electrical stimulation augments and enhances the absorption of the absorption enhancing agent of the invention.

Although as pointed out in the parent application an automatic injector device suitable for intramuscular self-administration of t-PA can be employed, the examples set forth below were performed by administering the t-PA and hydroxylamine hydrochloride directly into the muscle with a conventional needle and syringe. Administration of the agent with an automatic injector, however, it is believed will lead to even higher blood levels than those obtainable by manual injection.

After an approach employing intramuscular injection of t-PA with hydroxylamine (as the hydrochloride) and electrical stimulation of skeletal muscle at the injection site in rabbits had been found to yield peak blood levels of t-PA comparable to or exceeding those known to elicit coronary thrombolysis after intravenous infusion of t-PA in dogs and in patients, an analogous approach was evaluated in dogs subjected to coronary thrombosis. Facilitated absorption of t-PA after intramuscular injection was found to elicit coronary thrombolysis as well as therapeutic blood levels of t-PA in these feasibility experiments.

Large injectate volumes were employed because of the limited solubility of t-PA in conventional buffers. For consistency the volumes used in rabbits were selected to be similar to those planned for use in dogs (1 and 1.5 ml per injection site for rabbits and dogs respectively) even though they represented large volumes with respect to rabbit muscle mass. Thus the same concentration of absorption-enhancing agent per ml of injectate was used in both species even though they resulted in administration of markedly greater amounts of hydroxylamine per kg of body weight and a 10-fold lower concentration of t-PA in the injectates in rabbits compared with dogs despite administration of comparable proportion of t-PA administered per kg of body weight in the two species. Concentrating the t-PA appreciably with solubilizing agents such as thiocyanate it is believed will permit the volumes to be reduced substantially.

For studies in rabbits, the t-PA employed was either harvested from melanoma cell supernatant fractions (mt-Pa) as previously described (Bergmann, Science 220 1181–1183 (1983) or produced by recombinant DNA technology, Van der Werf, Circulation 69 605–610 (1984) (rt-PA, Genentech Corp., lot BH004 DAX). Results with the two preparations were indistinguishable and therefore the preparations were pooled. Concentrations of 0.5 mg t-PA per ml buffer (0.3 M NaCl, 0.01% Tween 80, 0.01M potassium phosphate buffer pH 7.5) were used. For studies in dogs, rt-PA (Genentech, lot TE031A) was concentrated 20-fold with an Amicon membrane filter system.

DMSO was used in 1% or 3% (v/v) solutions in vitro and in injectates. Hydroxylamine hydrochloride was used in concentrations of 43.75 mg per ml of t-PA solution. This concentration was compatible with a total hydroxylamine hydrochloride dose of approximately 13 mg/kg shown to be well tolerated physiologically.

To determine the extent to which the absorption-enhancing agents evaluated might interact with t-PA, solutions of rt-PA (0.015 to 50 ng/ml) were incubated at 37° C. for 1 hour after addition of 1% DMSO, 3% DMSO, 175 mg/ml hydroxylamine (as the hydrochloride), or both DMSO and hydroxylamine (as the hydrochloride). No effects were discernible on t-PA assayed innumoradiometrically or functionally.

Studies were performed in 56 nonfasted, white male New Zealand rabbits weighing approximately 2 kg. Endogenous t-PA in these animals does not react with antibody prepared against human t-PA and hence does not interfere with the immunoradiometric assay used to characterize blood levels of exogenously administered t-PA. Animals were anesthetized with sodium pentobarbital (24 mg/kg) and ventilated with 95% oxygen administered through a tracheostomy at 2 l/min. Skeletal muscle (vastus medialis) at the injection site was exposed bilaterally and serial blood samples were drawn through an indwelling femoral venous catheter. To augment skeletal muscle blood and lymph flow at the injection site, the muscle was stimulated for 2.0 msec at 14 volts with five pulses per second with two 27-gauge, 0.5 inch stainless steel needles. A single negative distal electrode was used as well. A total of 1 mg of t-PA/kg body weight was injected manually divided in 1 ml aliquots in each of 4 sites.

Coronary thrombosis was induced in fasted anesthetized dogs weighing approximately 23 kg, see Bergmann Science 220. 1181–1183 (1983). Occlusive thrombus formed within five to 10 minutes and was confirmed angiographically. Serial venous blood samples were obtained through an indwelling inferior vena caval catheter. Electrical field stimulation at the injection site was implemented with three 27-gauge stainless steel, one serving as the negative reference. Parameters were the same as those used in rabbits. t-PA was injected directly into exposed sartorius muscle in 1.5 ml aliquots per site such that the total dose was 3 mg/kg body weight and the total volume of injectate was 6 ml in aggregate for each dog.

The primary endpoint for experiments in the 56 rabbits studies was t-PA activity in blood. t-PA antigen levels were assayed serially as previously described Bergman, loc. cit. and Van der Werf, No. Engl. 2 Med. 310, 609–613 (1984). Functional t-PA activity was determined as well Bergman, loc. cit and Tiefenbrunn, Circulation 71, 110–116 (1985). Blood samples were obtained at 0° to 4° C. in sodium citrate vacutainer tubes before intramuscular injection of t-PA or vehicle alone, immediately after injection, and at selected intervals from one to 60 minutes subsequently.

For the feasibility experiments in dogs, an additional endpoint was coronary thrombolysis documented angiographically. Blood pressure, heart rate, the electrocardiogram, arterial blood gases and pH, hemoglobin and hemoglobin oxygen saturation were monitored.

For experiments in both species, a crude assessment of potential muscle injury at the site of injections was made by gross inspection. In addition, serial blood samples were assayed for plasma creatine kinase (CK) activity spectrophotometrically, Klein, Cardiovasc. Res. 7, 412–418 (1973) in view of the known prompt and marked liberation of CK into the circulation when skeletal muscle is inured.

Serial changes in blood levels of t-PA were evaluated in 56 rabbits comprising several groups. Blood levels were assessed before and at selected intervals after intramuscular injection of buffer with or without absorption-enhancing agent alone; or t-PA in buffer, buffer with DMSO, buffer with hydroxylamine (as the hydrochloride), or buffer with DMSO and hydroxylamine (as the hydrochloride).

The same combinations were evaluated with and without concomittant electrical stimulation of muscle at the injection site throughout the blood sampling interval. Once it had been determined that hydroxylamine facilitated absorption of t-PA, experiments were performed to define the dose-response relations for absorption of t-PA as a function to the concentration of t-PA and the concentration of hydroxylamine in the injectate. Possible systemic effects of hydroxylamine on absorption of t-PA wer assessed in rabbits by administering hydroxylamine without t-PA in two injection sites and t-PA without hydroxylamine in the other two sites.

The experiments performed in dogs were undertaken after it had been determined with rabbits therapeutic blood levels could be induced with amounts of t-PA/kg body weight (1 mg/kg) of the same order of magnitude as those that had been used previously for intravenous administration of t-PA in patients (0.5 to 0.75 mg/kg). Intramuscular t-PA was administered with hydroxylamine (as the hydrochloride) within five to 45 minutes after angiographic documentation of formation of an occlusive clot in the left anterior descending coronary artery, generally occurring within seven to 10 minutes after introduction of the thrombogenic coil into the vessel. Serial aniography was performed at approximately 15 minute intervals. Effects of t-PA on coronary thrombi correlated with plasma t-PA levels. After clot lysis (approximately 15 minutes after injection of t-PA), heparin (500 U/kg body weight) was given to prevent reocclusion. In the absence of exogenous activation of the fibrinolytic system, clots induced by the indwelling thrombogenic coronary arterial coil invariably persist despite administration of heparin (n =40 dogs).Statistical comparisons were performed by analysis of variance with Bonferroni critical limits or with Students test for paired data. Values are expressed as means ±SE.

Effects of Absorption-Enhancing Media on t-PA Activity in vitro

Neither hydroxylamine (as the hydrochloride) (175 mg/ml), 1% DMSO, 3% DMSO, nor concomitant hydroxylamine (as the hydrochloride) and DMSO modified immunoradiometrically detectable t-PA or functionally detectable t-PA activity in samples incubated for 1 hour at 37° C. containing 0.015 to 50 ng rt-PA.

Concentrations of t-PA in Blood

Prior to intramuscular injection of rt-PA, no human t-PA was detectable by immunoradiometric assay in plasma from any of the rabbits. No detectable endogenous t-PA activity was evident in plasma samples assayed with the fibrin plate functional assay despite the minor surgical procedure performed and the imposed electrical stimulation of muscle for 60 minutes in any of four rabbits tested. No human t-PA was detectable after injection of any of the combinations of vehicles tested when exogenous t-PA was not included in the injectate. No immunoradiometrically detectable t-PA was present in plasma samples from sham operated dogs during a 60 minute sampling interval with or without intramuscular injection of a total of 262 mg/ml of hydroxylamine as the hydrochloride administered in multiple sites. Fibrin plate assayable functional activity in sham operated dogs ranged from 10 to 53 IU/ml and did not increase in any of four animals tested during the 60 minute sampling interval after electrical stimulation and intramuscular injection of hydroxylamine hydrochloride in buffer without t-PA.

In control experiments with hydroxylamine hydrochloride alone (262 mg) injected intramuscularly in dogs, peak methemoglobin levels ranged from 11 to 13% and occurred within five to 15 minutes after intramuscular injection (n =3). Arterial oxygen tension decreased to a minimum of 93 mm Hg. Hemoglobin saturation with oxygen declined to a minimum of 81%. Except for transitory acceleration of heart rate, dogs given hydroxylamine hydrochloride with or without t-PA exhibited no significant hemodynamic or electrocardiographic abnormaliites.

In the Drawings:

FIG. 3 is a chart showing peak plasma t-PA activity as a function of the amount of t-PA administered intramuscularly in 6 rabbits. Conditions were the same as those indicated in the legend to FIG. 1 except that the total amount of t-PA administered was varied as indicated. Panel A depicts immunoradiometrically detectable activity; panel B depicts amidolytic, functional activity. Dose related differences throughout the 1 hour interval of measurement for the entire time-activity aerol (n=30 determinations) were significant as determined byanalysis of variance (p <0.001).

FIG. 5 a graph of serial changes in plasma t-PA assayed immunoradiometrically in a dog which had been subjected to coronary thrombosis. Thrombosis was induced with a thrombogenic coil advanced into the left anterior descending coronary artery at the tip of a coronary arterial catheter. Coronary thrombolysis was induced by facilitated absorption of intramuscularly administered t-PA. (The thrombogenic coil elicited formation of a clot evident by lack of distal fill with angiographic dye as well as by lack of opacification of the vessel proximal to the coil that appears as a bright rectangle.) Fifteen minutes after intramuscular administration of t-PA (3 mg/kg in a total injectate volume of 6 ml divided among four sites) and electrical stimulation of muscle at the injection site, lysis of the clot proximal and distal to the coil was evident with angiographically demonstrable restoration of patency. As can be seen, plasma t-PA activity peaked soon after facilitated absorption of intramuscularly administered t-PA. Elevated levels persisted throughout the sampling interval. A secondary peak was seen in each of the three dogs studied.

Blood Levels of t-PA After Intramuscular Injection In Rabbits

Figure 1:
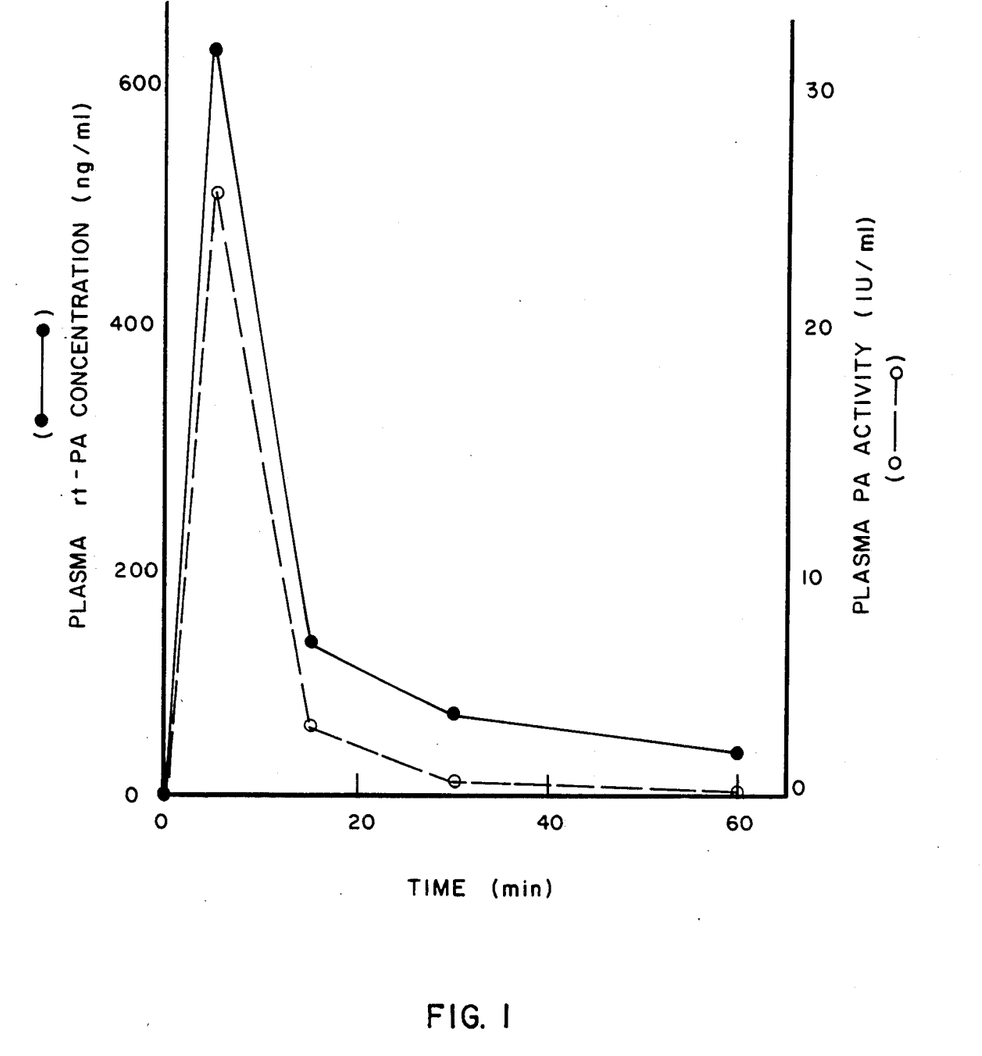
FIG. 1 is a graph of immunoradiometrically detectable and functionally active plasma t-PA activity in plasma samples from a rabbit injected with 2 mg t-PA buffer with 43.75 mg/ml hydroxylamine hydrochloride (total injectate volume=4 ml divided among 4 sites) followed by electrical stimulation at the injection sites throughout the sampling interval. Both immuno-reactive and functionally active t-PA peaked rapidly after intramuscular injection with facilitated absorption.

As shown in Table 1, t-PA injected in buffer alone increased blood levels only minutely. The addition of DMSO to the injectate did not increase t-PA levels in plasma. In contrast, hydroxylamine hydrochloride augmented absorption of t-PA yielding peak blood levels five minutes after injection approximately 40-fold higher than those seen in its absence. An example of serial changes of immunoradiometrically and functional t-PA activity assayed with fibrin plates after intramuscular absorption of t-PA facilitated by inclusion of hydroxylamine hydrochloride in the injectate and electrical stimulation of muscle at the injection site is shown in FIG. 1.

TABLE 1

| Immunoradiometrically Detectable t-PA In Plasma (ng/ml) After Intramuscularly Administered t-PA | | | |
|---|---|---|---|
| Interval After Injection (min) | t-PA In Buffer Alone (n = 6) | t-Pa in Buffer + 3% DMSO (n = 6) | t-PA in Buffer + Hydroxylamine Hydrochloride (n = 15) |
| 0 | 0 ± 0 | 0 ± 0 | 0 ± 0 |
| 5 | 8 ± 2 | 11 ± 4 | 431 ± 52* |
| 15 | 9 ± 2 | 8 ± 2 | 146 ± 16* |
| 30 | 9 ± 2 | 9 ± 1 | 85 ± 17* |
| 60 | 10 ± 3 | 10 ± 1 | 53 ± 11* |

Values are means ± SE. All injectates contained 2 mg t-PA in an aggregate of 4 ml (1 ml per site). The concentration of hydroxylamine hydrochloride was 43.75 mg/ml. All experiments tabulated were performed with electrical stimulation of muscle at the infarction site.
*= $P < .01$ compared with t-PA in buffer alone or in buffer + DMSO To determine whether augmentation of muscle blood flow by electrical stimulation would enhance absorption of t-PA administered intramuscularly, experiments were performed with and without electrical stimulation after injection of t-PA in buffer alone, t-PA in buffer supplemented with DMSO, and t-PA in buffer supplemented with hydroxylamine hydrochloride. The very low blood levels seen when t-PA wa administered without hydroxylamine hydrochloride were not consistently modified by electrical stimulation (n=11 animals). However, in animals given t-PA with hydroxylamine hydrochloride (n=15) stimulation augmented peak levels by an average of 258±32% without altering the time course of absorption or clearance of t-PA.

Figure 2:
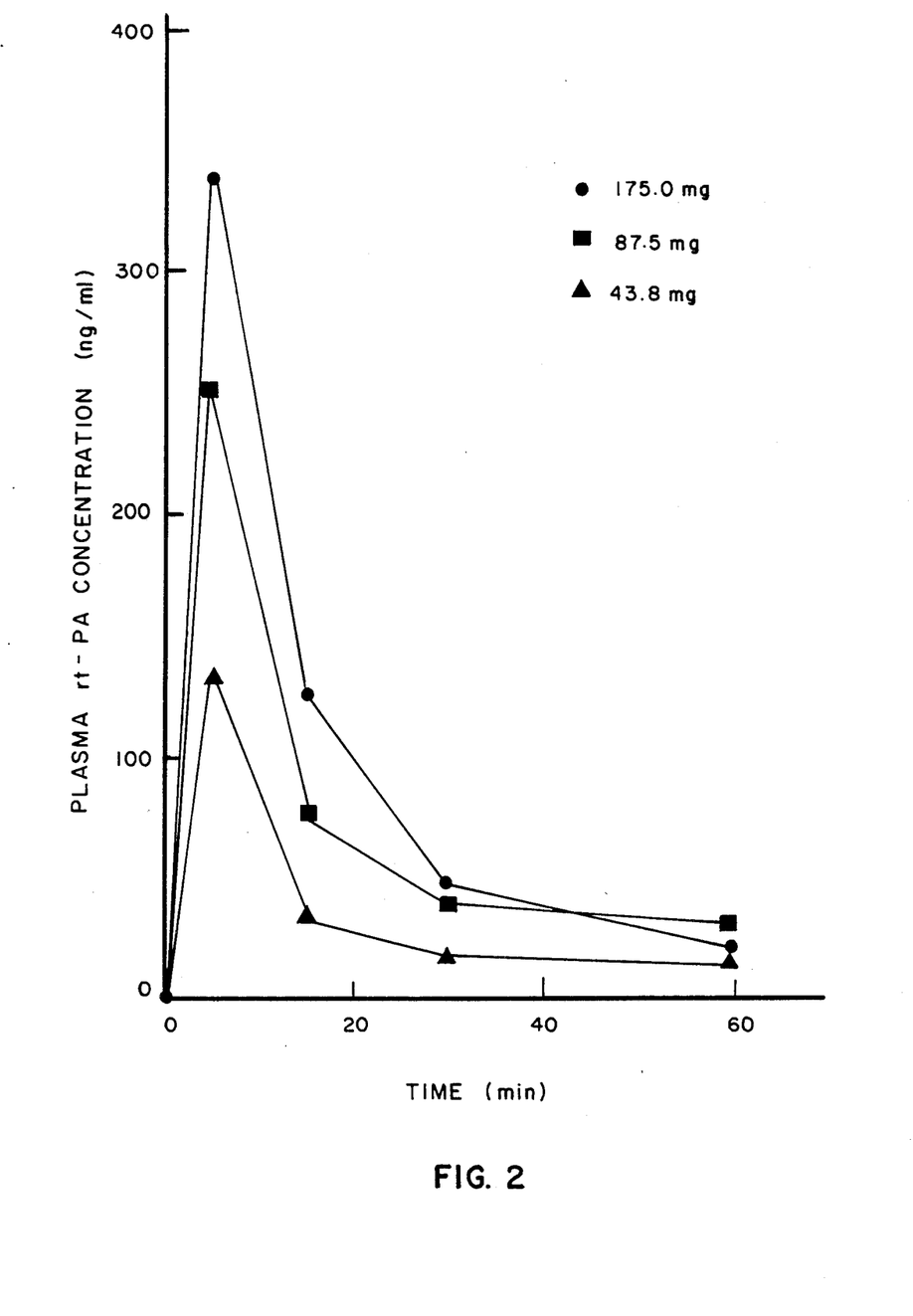
FIG. 2 is a graph showing the dependence of the peak concentration plasma of immunoradiometrically detectable t-PA on the concentration of hydroxylamine in the injectate. Conditions were the same as those indicated in the legend to FIG. 1 except that the amounts of hydroxylamine hydrochloride in the 4 ml aggregate volume of injectate were varied as indicated in the figure.
Figure 3:
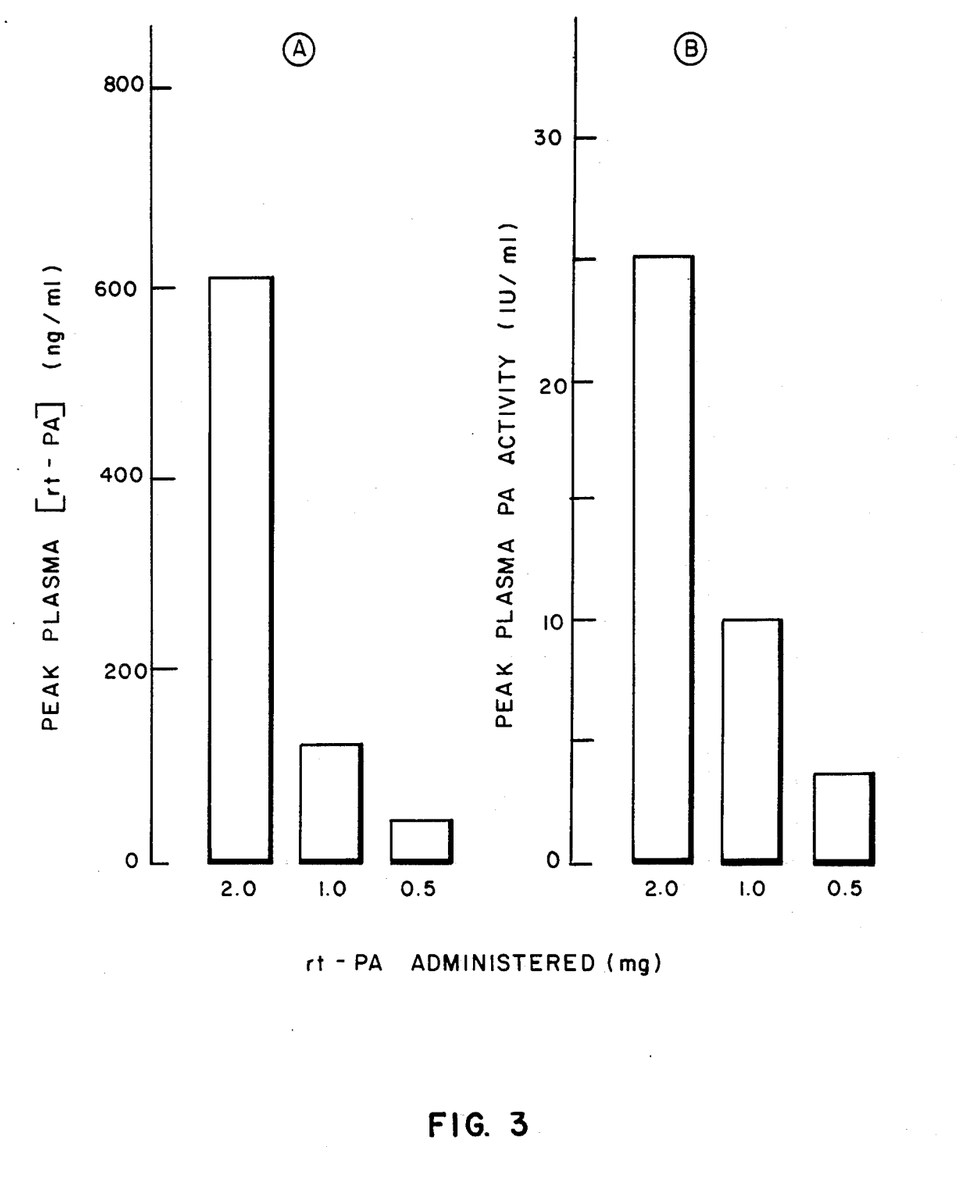
Figure 4:
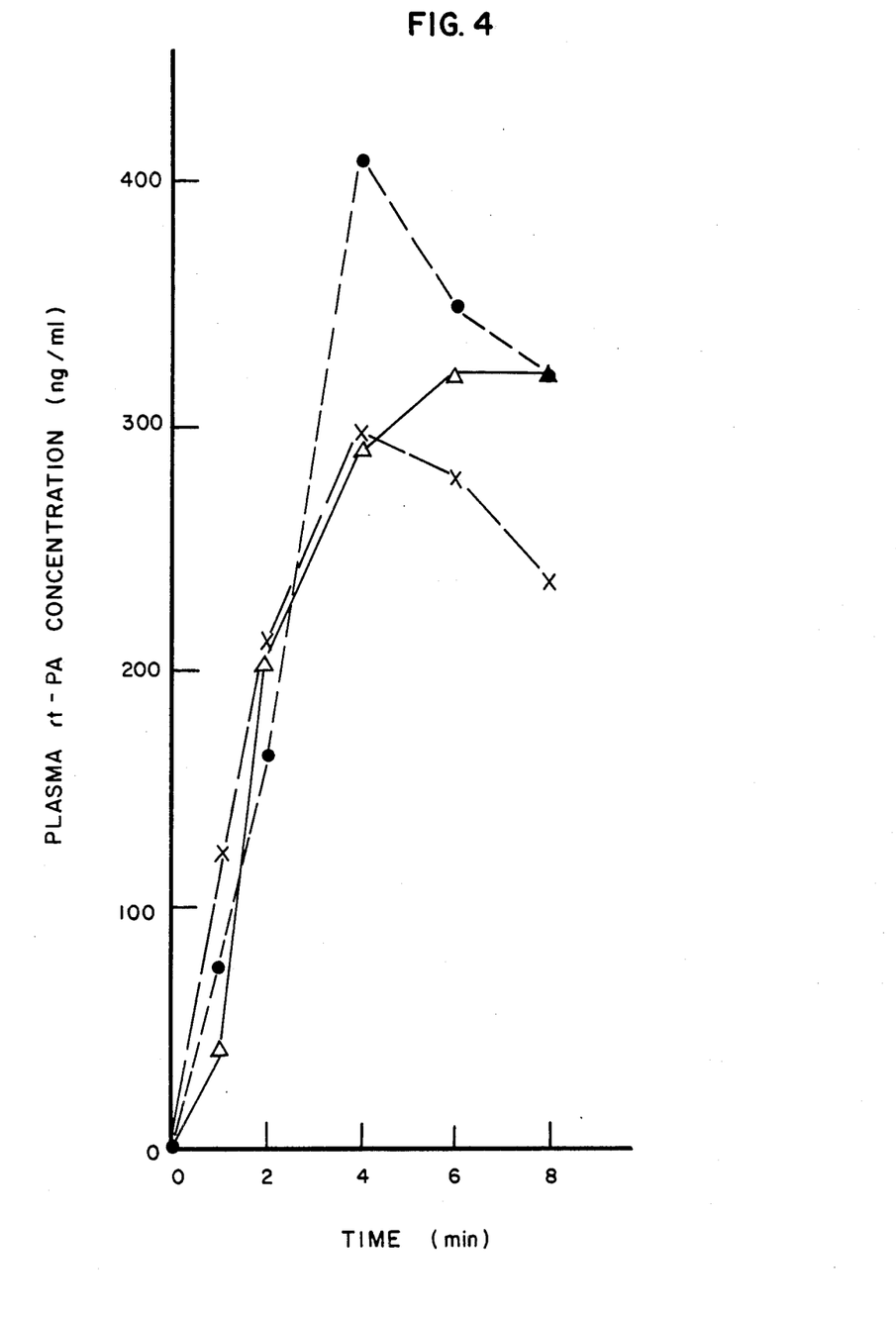
FIG. 4 is a graph showing early changes in plasma t-PA concentrations after facilitated absorption of intramuscularly administered t-PA in each of three rabbits. Conditions were the same as those indicated in the legend to FIG. 1.

As shown in FIG. 2, immunoradiometrically detectable t-PA peak blood levels were proportional to the amount of hydroxylamine hydrochloride in the injectate. Addition of 1% or 3% DMSO to hydroxylamine (as the hydrochloride) - enriched injectates did not increase peak blood levels of t-PA compared with results with hydroxylamine hydrochloride alone when the amount of t-PA was held constant. Both immunoradiometrically detectable and functionally active t-PA after administration of exogenous t-PA were proportional to the concentration of t-PA over a four-fold range when the amount and concentration of hydroxylamine hydrochloride in the injectate were held constant (FIG. 3). As can be seen in FIG. 4, blood levels rose rapidly and peaked between 4 and 5 minutes after injection. Appreciable concentrations of t-PA in plasma were evident as early as one minute after intramuscular injection in each case.

The augmentation of peak plasma t-PA after facilitated absorption with hydroxylamine hydrochloride was not caused simply by the decreased pH of the injectate. In each of two animals, the pH of the injectate was titrated to 5.9 without hydroxylamine. Plasma t-PA concentration five minutes after injection was only 6 ng/ml. No significant increase occurred subsequently. The increment seen with hydroxylamine hydrochloride was not attributable simply to systemic effects of hydroxylamine hydrochloride. In two animals in which hydroxylamine was injected into the right and t-PA in buffer into the left thigh muscle, peak blood levels did not exceed those in Table 1 for t-PA injected in buffer alone.

Although the amounts of absorptionenhancing agent per kg body weight used in rabbits were considerably greater than those used in dogs or anticipated ultimately for possible clinical studies, the excessively large quantities were employed to determine whether high concentrations in the injectate would be deleterious to skeletal muscle. In rabbits, plasma CK was not significantly different 30 minutes after the surgical procedure, injection of t-PA with hydroxylamine hydrochloride and electrical stimulation compared with values after injection of buffer alone under the same conditions (690±82 compared with 696±63 IU/l). In dogs given 175 mg hydroxylamine hydrochloride with or without t-PA, plasma CK increased by less than 18% of baseline at the completion of the study. No hematoma were evident by gross inspection. Light microscopy of sections from the injection site obtained two hours after injection delineated only scanty interstitial hemorrhage and inflammation.

Figure 5:
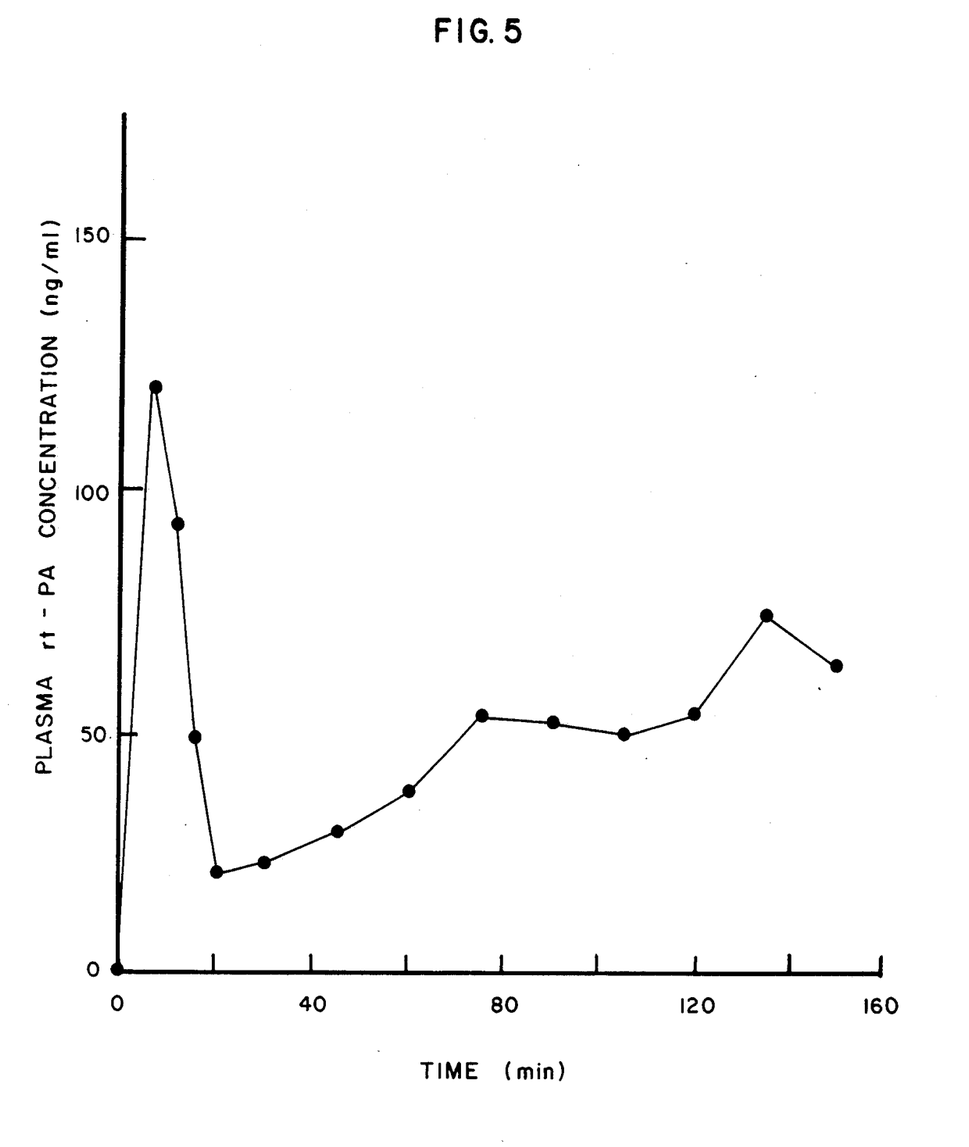

Effects of Facilitated Absorption of Intramuscularly Administered t-PA on Coronary Thrombolysis in Dogs After demonstrating that facilitated absorption of t-PA could be achieved in rabbits with hydroxylamine hydrochloride in the injectate, pilot studies were performed in dogs to determine whether the approach developed could elicit coronary thrombolysis. Arterial blood pressure after injection of hydroxylamine hydrochloride intramuscularly witn (n=3) or without (n=3) t-PA declined only modestly (from an average of 166/121 mm Hg to 144/104) reaching a minimum 2 minutes after injection. Heart rate increased transiently by an average of 32% peaking also 2 minutes after injection. Ventricular arrhythmias did not occur with hydroxylamine hydrochloride alone. Intramuscularly administered t-PA (3 mg/kg) followed by electrical stimulation initiated coronary thrombolysis within 15 minutes heralded by reperfusion arrhythmias. Similar results were obtained in each of the three animals studied. Plasma t-PA values followed a similar time course but were lower than those seen in rabbits. The differences may reflect species differences i the absorption or clearance of human rt-OA or the larger ratio of injectate volume to muscle mass in rabbits. In addition, as shown in FIG. 5, a secondary peak of immunoradiometrically detectable t-PA occurred beginning approximately 40 minutes after the first peak in each dog compatible with lat release from the skeletal muscle depot because of changes in blood flow or slow lymphatic transport of t-PA into the circulation among other possibilities.

Thus it has been found that therapeutic blood levels of functionally active t-PA can be achieved and that coronary thrombolysis can be eliicted by facilitated absorption of intramuscularly injected material. Plasma activity peaked within five minutes after injection and subsequently declined rapidly, consistent with the known half-life of t-PA in the circulation. The blood levels obtained were sufficient to induce coronary thrombolysis in dogs within 15 minutes despite the continued presence of an indwelling, coronary, thrombogenic coil. Absorption of t-PA was enhanced by inclusion of hydroxylamine in the injectate and by augmentation of skeletal muscle blood flow by electrical stimulation. Gross injury to skeletal muscle did not occur.

Because low levels of t-PA in plasma may be adequate to induce clot lysis of nascent thrombi judging from results of studies in vitro and because the biological half-life of t-PA bound to fibrin is substantially longer than the half-life of circulating t-PA, see Brommer, Thromb. Res. 34, 109–115 (1984), Tran-Thang, Blood 63 1331–1337 (1984), Bergmann, Circulation 70 II:108 (Abstract) (1984), it is believed that coronary thrombolysis early after the onset of thrombosis in vivo may be obtained with lower quantites of t-PA, hydroxylamine hydrochloride, or both than those used in the examples set forth above. Reduction of the injectate volume would diminish the dose of hydroxylamine or other absorption enhancing agent required and minimize potential injury to muscle at the injection site.

To date, t-PA and other activators of the fibrinolytic system have been given only by direct injection into the blood stream. This invention provides an alternative means of administration of t-PA potentially amendable to prompt implementation by paramedical personnel or by telephonically supervised patients at high risk previously instructed in self-medication procedures.

Hydroxylamine was employed after numerous attempts with other absorption-enhancing media for other compounds failed to yield the desired results with t-PA. Its major side effect, induction of methemoglobinemia does not prohibitively limit tissue oxygenation with the doses used. If the concentration of the hydroxylamine in the injectate is the critical determinant of absorption of t-PA as appears likely judging from the present results, the total dose of hydroxylamine required in human subjects is likely to be so low that induced methemoglobinemia would be of only trivial extent even for patients with ischemic heart disease especially if the injectate volume can be reduced further by increasing the concentration of t-PA. In those cases where the methemoglobinemia accompanying use of this absorption-enhancer is deemed to be unacceptably severe, adjuvant measures such as concomitant administration of methylene blue or glutathione might be utilized to minimize or obviate the problem, see Layne, J. Pharmacol. Exp. Therap. 165, 36–44 (1969).

Blood levels of t-PA comparable to those obtained in the present investigation induce coronary thrombolysis in experimental animals and patients without inducing a systemic lytic state predisposing to bleeding. The time course of elevation of plasma t-PA after facilitated intramuscular absorption is particularly favorable because of its sharp peak. With the envisioned application of an appropriate regimen, subjects would be under direct medical care soon after self-medication with an automatic injector or treatment by relatives of paramedical personnel. Thus, as the blood levels declined promptly after intramuscularly administered t-PA had been given, intravenous infusions could be initiated along with anticoagulants or other measures taken to prevent reocclusion while definitive diagnostic information wa being obtained.

The possibility that myocardial reperfusion induced by facilitated absorption of intramuscularly administered t-PA might give rise to reperfusion arrhythmias is easily managed in the setting of the cardiac catheterization laboratory or coronary care unit but can be potentially dangerous in the medically unattended patient. Thus, there is advantage in the concomitant administration of an antifibrillatory or anti-arrhythmic agent such as lidocaine or an alpha-adrenergic blocking agent as set forth in the parent application.

It has also been found that to prevent reocclusions or platelet aggregation it is desirable to either:

1. inhibit synthesis of thromboxane A *thromboxane $A_2$) with a thromboxane synthetase inhibitor, e.g. an imidazole such as 4-(2-[1H-imidazol-1-yl]ethoxy)-benzoic acid hydrochloride (dazoxiben)

2. introduce an antagonist for the receptor of the thromboxane A (thromboxane $A_2$) such as [1$\alpha$, 2$\beta$(5Z), 3$\beta$(1E), 4$\alpha$]-7-[3-(3-cyclohexyl-3-hydroxy-1-propenyl)-7-oxabicyclo[2.2.1]hept-2-yl]-5-heptenoic acid)(SQ 27,427)

3. introduce another inhibitor of platelet aggregation, e.g. aspirin, indomethacin, naproxin, and sulfinpyrazone.

The agent for the prevention of reocclusions or platelet aggregations could be administered simultaneously or sequentially in either order with reference to the t-PA and absorption enhancing agent, e.g. hydroxylamine hydrochloride. The agent for the prevention of reocclusions or platelet aggregations can be administered in conventional manner, e.g. intramuscularly, intravenously, or even orally.

The receptor antagonist or other agent for prevention of platelet reocclusions can be administered for example in an amount of 0.1–10 mg/kg body weight.

What is claimed is:

1. A method of increasing the absorption of t-PA in the blood in a mammal in need of t-PA therapy comprising administering to the mammal an amount of t-PA inhibitor disassociating agent effective to increase the disassociation of the inhibitor from the t-PA, the amount of exogenous t-PA being less than that required to be administered in the absence of the inhibitor disassociating agent.

2. A method according to claim 1 wherein the inhibitor dissociating agent is added intramuscularly.

3. A method according to claim 1 wherein the inhibitor disassociating agent is added intravenously.

4. A method according to claim 1 wherein the inhibitor disassociating agent is hydroxylamine or a non-toxic salt thereof.

5. A method according to claim 4 wherein the inhibitor dissociating agent is added intramuscularly.

6. A method according to claim 4 wherein the inhibitor disassociating agent is added intravenously.

7. A method according to claim 4 wherein the inhibitor disassociating agent is hydroxylamine hydrochloride.

* * * * *